Figure 1:
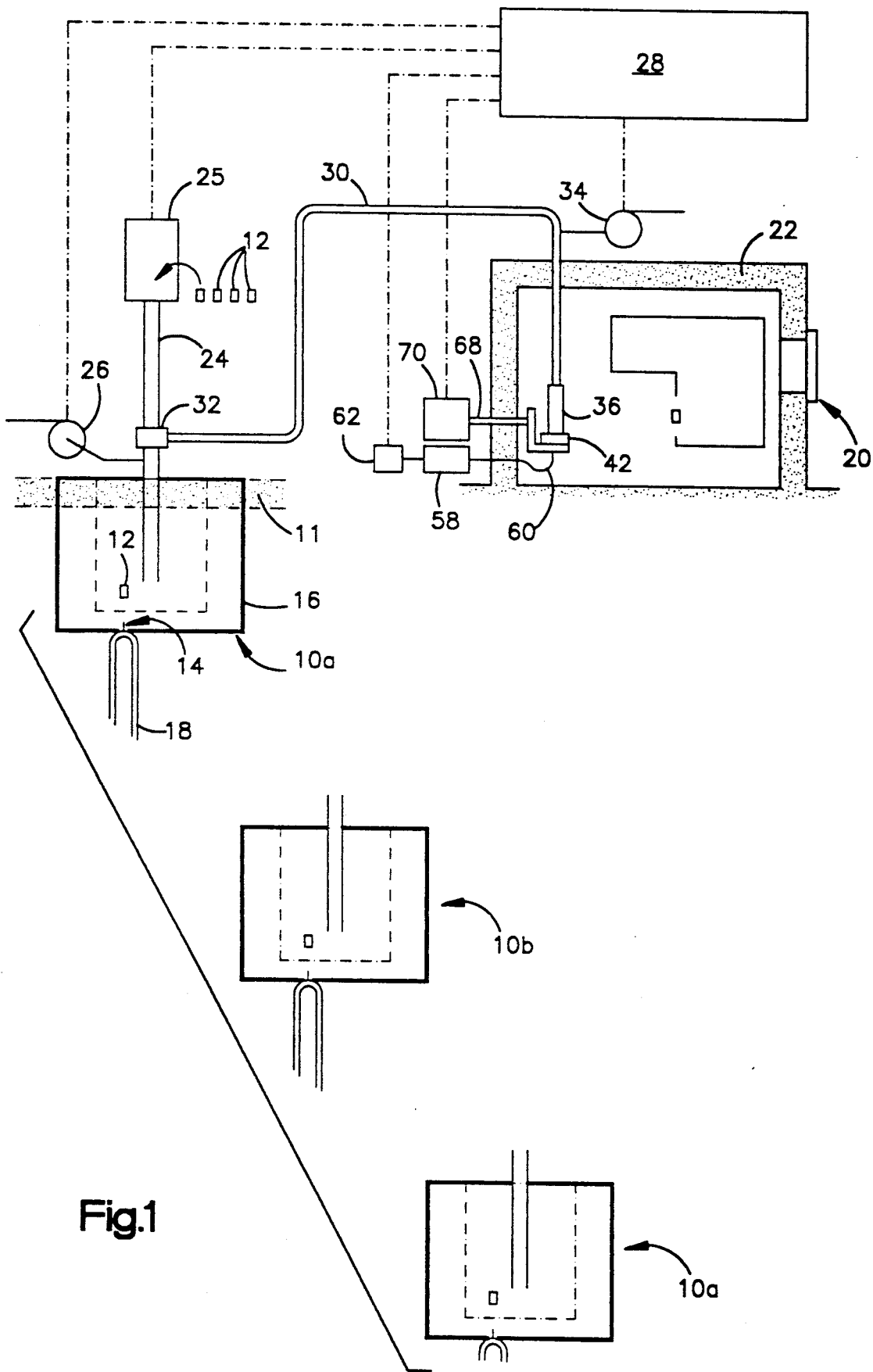

United States Patent [19]

Besnier et al.

[11] Patent Number: 5,280,140
[45] Date of Patent: Jan. 18, 1994

[54] AUTOMATED INSTALLATION FOR THE TRANSFER AND WEIGHING OF POTS CONTAINING A RADIOACTIVE LIQUID BETWEEN A SAMPLING UNIT AND AN ANALYSIS CHAIN

[75] Inventors: Joseph Besnier, Beaumont Hague; Jean-Francois Gey; Denis Ferron, both of Equeurdreville, all of France

[73] Assignee: Cogema-Compagnie Generale Des Matieres Nucleaires, France

[21] Appl. No.: 866,152

[22] Filed: Apr. 9, 1992

[30] Foreign Application Priority Data

Apr. 17, 1991 [FR] France .................. 91 04739

[51] Int. Cl.⁵ .................. G01G 19/00; G01G 23/00
[52] U.S. Cl. .................. 177/145; 177/245
[58] Field of Search .................. 177/145, 245

[56] References Cited

U.S. PATENT DOCUMENTS 4,470,265 9/1984 Correia .
4,516,436 5/1985 Conche et al. .................. 73/863.85
4,528,848 7/1985 Hafner .................. 177/16 X

FOREIGN PATENT DOCUMENTS 311229 4/1989 European Pat. Off. .
364078 4/1990 European Pat. Off. .
661120 6/1987 Switzerland .
2200469 8/1988 United Kingdom .

Primary Examiner—George H. Miller, Jr.
Attorney, Agent, or Firm—Pearne, Gordon, McCoy & Granger

[57] ABSTRACT

In an installation designed for pneumatically transferring pots (12) between a sampling unit, in which these pots are filled with a radioactive liquid sample and an analysis chain or line protected by an enclosure, with the receptacle (36) by which the pots enter the chain or line, is associated a force transducer (42). In conjunction with an electronic measuring means located outside the said enclosure, said transducer weighs the pots and makes it possible to detect when one of them is empty or inadequately filled. An ejection nozzle (66) connected to a compressed air source discharges the pot when it is weighed.

10 Claims, 3 Drawing Sheets

AUTOMATED INSTALLATION FOR THE TRANSFER AND WEIGHING OF POTS CONTAINING A RADIOACTIVE LIQUID BETWEEN A SAMPLING UNIT AND AN ANALYSIS CHAIN

The invention relates to an automatic installation for transferring pots between one or more sampling units ensuring the automatic introduction of a radioactive liquid sample into each pot and one or more analysis lines or chains, surrounded by a biological protection enclosure, said installation also making it possible to weigh the pots during their transfer.

In nuclear fuel processing plants, it is desirable to be able to sample at different points radioactive liquids. The samples taken make it possible to carry out analyses, whose results permit intervention on the processing operation taking place in order to modify certain parameters thereof.

In practice and as described in FR-A-2,515,350, sampling takes place in plastics material pots, which are placed in containers known as sliders, whose special shape aids the transfer of the pots into tubes under the action of pneumatic transfer means. Each pot is sealed by a cap or lid and is previously placed under a vacuum.

The above document also shows that samples are taken in sampling units within which the cap sealing each of the pots is engaged on a sampling needle, whose opposite end is connected by an appropriate circuit to the point of the plant where it is wished to take the sample. More specifically, each sampling unit has several needles linked by independent circuits with different parts of the plant, so that several different radioactive liquid samples can be successively taken on the same sampling unit. The actual sampling is carried out by the suction of the liquid through the needle under the effect of the vacuum initially present in the pot.

In an installation of this type, the pots containing the samples taken are pneumatically transferred to one or more analysis chains in confined enclosures, the tube used for transferring the pots traverses each of the enclosures in a substantially vertical direction, so that the pots drop by gravity into a receptacle located within the enclosure. This receptacle has a slide ring insulating the pneumatic circuit from the interior of the enclosure when a pot is not admitted into the latter.

When such an installation is automated, the situation may arise where an empty pot or a pot containing an inadequate liquid quantity for carrying out an analysis is transferred to the analysis chain. The radioactive liquid which should have been present in the pot cannot then be analysed. It is then necessary in order to carry out a new sampling operation, to make a new analysis request and the response time is too long. It is therefore desirable to be able to check the filling state of each of the pots transferred from the sampling units to the analysis chains, e.g. in order to make it possible to carry out a new sampling operation corresponding to that which is missing within the shortest possible time.

Moreover, when the analyses have been made, all the sampled radioactive liquid and all the pots used for the sampling operations constitute waste, which have to be processed in accordance with the conventional radioactive waste processing procedures. For this reason, it is desirable to limit to the greatest possible extent the sampled radioactive liquid quantity, as well as the number of pots used. This makes it necessary to be able to check the volume of each of the samples taken, in order that the said volume precisely corresponds to the analysis or analyses to be carried out on said liquid. This also makes it necessary to preferably use a single pot, when the sampled liquid volume necessary for several analyses can be contained therein.

The invention mainly relates to an automated pot transfer installation, whose original design makes it possible both to detect the presence of an empty or inadequately radioactive liquid-filled pot and authorize a stricter check on the sampled liquids leading to a reduction in the amount of waste constituted by said liquids and the pots when the analyses are ended.

Moreover, it is important to note that such a result must, as far as possible, be obtained without increasing the transfer time of the pots from each sampling unit to the analysis chain and without modifications made to the transfer installation requiring the installation of an expensive supplementary biological protection leading to an irradiation risk for personnel in the case of an intervention involving the removal of said biological protection due to a system failure.

The invention also relates to an automated pot transfer installation, in which the checking operations carried out on each of the pots are performed substantially without increasing the transfer time of the pots and without requiring a supplementary biological protection, which can lead to extra costs and irradiation risks for personnel in the case of an intervention.

Finally, the invention also relates to a pot transfer installation in which these different results are obtained in a completely automated manner, so as to limit to the greatest possible extent the number of operators and so as not to increase the transfer time.

According to the invention, these different results are obtained by means of an automated installation for the transfer of pots between at least one sampling unit ensuring the automatic introduction of a radioactive liquid sample into each pot, and at least one analysis chain or line surrounded by a confined enclosure, said installation being characterized in that it comprises tubes connecting each processing unit to a receptacle placed within the enclosure of each of the analysis chains, pneumatic means for the transfer of pots into said tubes, a central unit controlling the sampling unit and the pneumatic transfer means and pot weighing means associated with each of the receptacles.

In an installation defined in this way, the weighing means can make it possible to check the emptiness state of certain of the pots. For this purpose, these weighing means are associated with comparison means, which compare a measuring signal supplied by the weighing means with a given threshold and then address an emptiness signal to the central unit when the measuring signal is below this threshold. Advantageously, the central unit then controls a further sampling identical to the missing one, on receiving such an emptiness signal.

Moreover, the informations supplied by the weighing means can also be used directly in order to calculate the liquid volume contained in each of the pots, the density of said liquid being known for each of the sampling points in question. A stricter control of the sampling operations can then be envisaged, which leads to a significant reduction in the liquid quantity discarded after analysis, as well as the quantity of solid waste constituted by the pots.

It should also be noted that the installation of the weighing means on the receptacles placed within the biological protection enclosures of each analysis chain makes it unnecessary to add any supplementary biological protection. The extra costs resulting from such an addition are consequently avoided. Moreover, an intervention can optionally take place, in the case of a failure, directly in the analysis chain, using remote handling means usually equipping the latter. Therefore such an intervention leads to virtually no irradiation risk for personnel.

In addition, the installation of the weighing means on the receptacles of the analysis chains makes it possible, by adding to the installation means for automatically ejecting the pots following their weighing, to cause virtually no increase in the pot transfer time. In practice, said ejection means can be constituted by an ejection nozzle mounted on each of the receptacles and connected to a compressed air source controlled by the central unit.

According to a first embodiment of the invention, the weighing means incorporate a force transducer fitted to the lower end of a substantially vertically axed slide ring constituting the receptacle.

According to a second embodiment of the invention, the weighing means incorporate a force transducer fitted to a fixed support, below a funnel or hopper integral with a substantially vertically axed slide ring constituting the receptacle, the funnel being laterally downwardly displaced with respect to the slide ring, the latter having a lower ramp oriented towards said funnel.

In each of these embodiments, the force transducer advantageously has a lower reference part and a vertically mobile upper part with respect to said lower part and which can bear against top and bottom abutment surfaces of the lower part when a force exceeding a tolerance threshold of the transducers is respectively exerted upwards or downwards on the upper part. This characteristic enables the force transducer to withstand the shocks, which may be produced by filled pots arriving at high speed and dropping by gravity.

According to a special arrangement for the nuclear industry, an electronic measuring means associated with the force transducer is located outside the confined enclosure of the analysis chain and connected to the transducer by a cable passing through said enclosure.

In the case where the pots are made from a material which can be charged with static electricity, such as a plastics material, the discharge of said static electricity on the plate or disk of the weighing means used for receiving the pots could lead to an erroneous measurement. To obviate this disadvantage, it is either possible to make at least the surface of said disk from an electrically insulating material, or to provide means for discharging the static electricity carried by the pots into the receptacle above the weighing means.

The invention is described in greater detail hereinafter relative to two non-limitative embodiments and with reference to the attached drawings, wherein show:

FIG. 1 very diagrammatically a pot transfer installation according to the invention.

Figure 2:
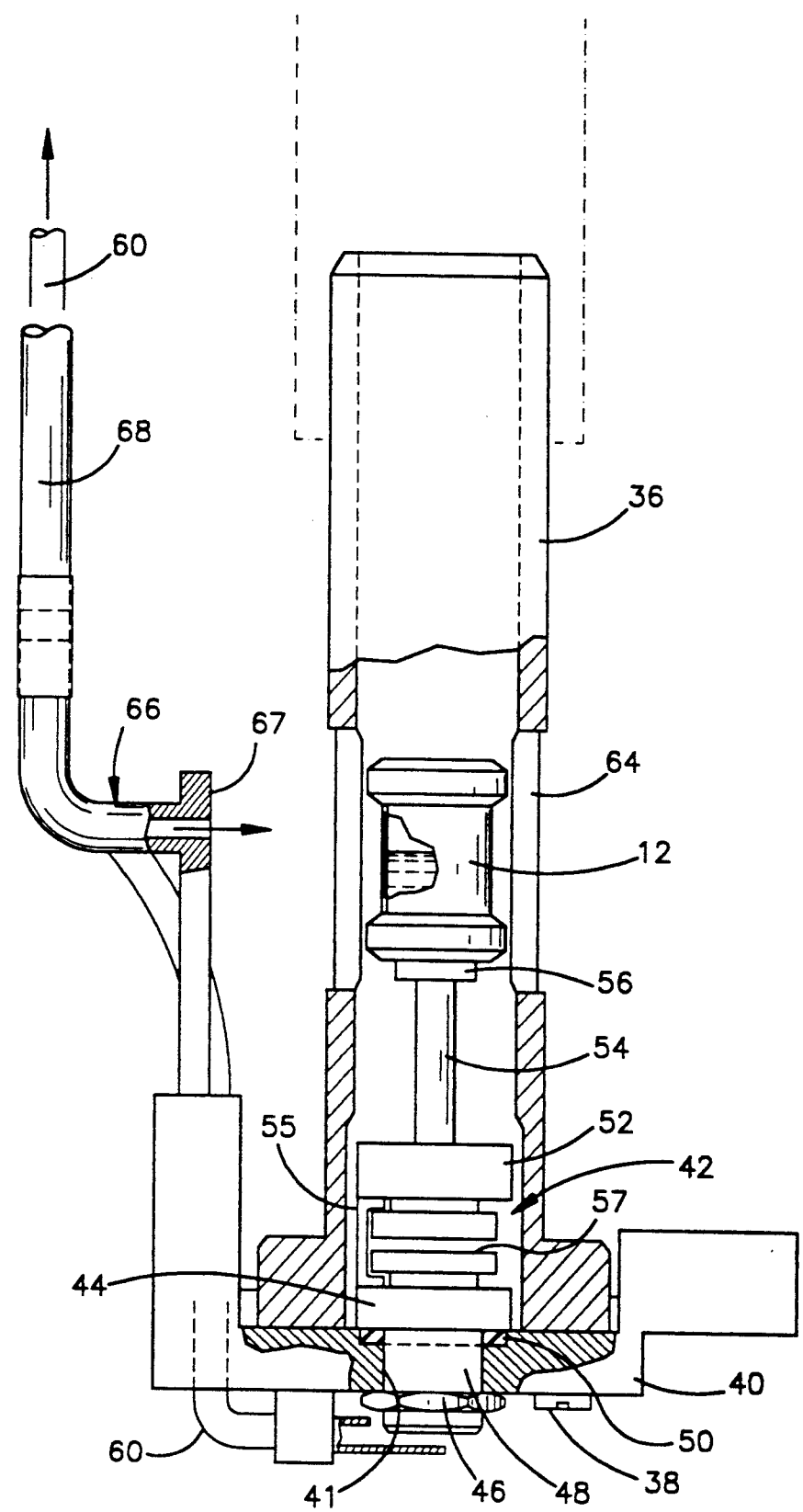

FIG. 2 a part sectional view illustrating on a larger scale the receptacle fitted in the enclosure of each analysis chain for receiving pots containing samples taken, as well as the force transducer associated with said receptacle in order to ensure the weighing of each pot in accordance with a first embodiment of the invention.

Figure 3:
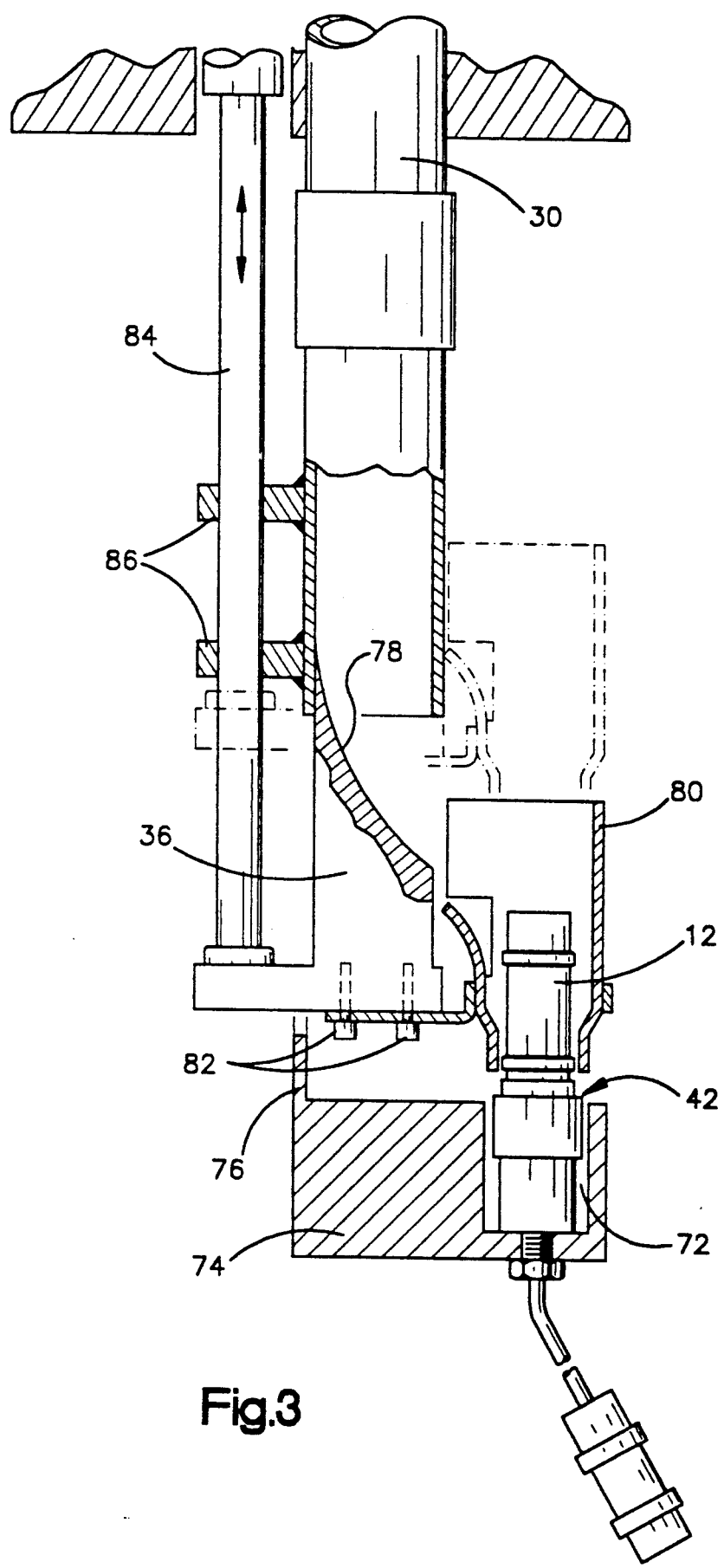

FIG. 3 a sectional view comparable to FIG. 2 diagrammatically illustrating a second embodiment of the invention.

In FIG. 1 references 10a,10b and 10c designate in general manner sampling units in which the pots 12, which are initially under vacuum, are in turn filled in an automatic manner with radioactive liquid samples from different points of a nuclear fuel processing plant.

Each of the sampling units 10a,10b,10c, whose number can vary according to the number and distribution of the points in the plant where sampling is to take place, can in particular be produced in the manner described in FR-A-2,515,350.

For the satisfactory understanding of the invention, it is merely pointed out that the sampling units 10a,10b and 10c have not shown, remotely controlled handling means, by means of which a vacuum pot 12 traverses a slab 11 defining the contaminated area, in order to penetrate a tank 16 of the sampling unit. The handling means then position the pot above a needle 14 chosen in accordance with a predetermined program as a function of the analyses to be carried out from among a certain number of needles projecting into the bottom of the tank 16, after which the pot is engaged on said needle. A liquid sample is then automatically sucked into the pot under the effect of the vacuum initially prevailing within the latter. Thus, the lower end of the needle 14 is then immersed in a container in which the radioactive liquid to be sampled is supplied by a circuit 18, branched to the point of the processing plant where sampling is to take place. An embodiment of the circuit 18 is described in FR-A-2,516,242.

The pots 12 in which the sampling operations take place can in particular be manufactured in the manner described in FR-A-2,515,350. In this case, each pot consists of a plastics material bottle, sealed by an elastomer cap, so as to form the actual pot, as well as a plastics material outer envelope, referred to as a slider and whose profile is known, so as to permit a pneumatic transfer of the pots into tubes. The pot appears in the sampling unit with its cap oriented downwards, in such a way that it is the said cap which is engaged on the needle 14.

As a variant, each of the pots 12 could be produced without an outer envelope, the bottle then having an external shape identical to that of the slider in the preceding case.

FIG. 1 also diagrammatically shows the installation permitting the transfer of the empty pots up to each of the sampling units 10a,10b, 10c, followed by the transfer of the pots containing the samples up to one or more analysis chains 20, whereof only one is illustrated in the drawing in order to facilitate the understanding thereof. Each analysis chain 20 is defined by a confined biological protection enclosure 22.

The pot transfer installation firstly comprises tubes 24, into which the empty pots 12 are transferred from one or more distribution stations 25 of said empty pots 12 up to each of the sampling units 10a, 10b,10c. The successive transfer of each of the pots 12 into the tubes 24 is ensured by pneumatic means, which comprise a suction pump 26 connected to the inlet of each of the sampling units. Each pump 26 is controlled, in the same way as the handling means for the pots 12 associated with each of the sampling units and the pot distribution station 25, by a central control unit 28.

The pot transfer installation according to the invention also comprises tubes 30, which connect each of the sampling units 10a,10b,10c to each of the analysis chains 20. The tubes 30 are equipped with not shown switches, which are also controlled by the central control unit 28, which make it possible to direct in a random, automated manner each of the pots 12 from a random sampling unit 10a,10b,10c to one or other of the analysis chains, so that the necessary analyses can be carried out on a sample taken.

If the removal of the pots from the sampling units takes place by the same path by which they have entered, switches 32, also controlled by the central control unit 28, are placed between the tubes 24 and 30, in the manner illustrated in FIG. 1.

The transfer of the pots 12 containing the samples taken from the sampling units into the analysis chains takes place by pneumatic means, e.g. having vacuum pumps 34, controlled by the central control unit 28 and branched to the tubes 30, at the entrance to each of the analysis chains 20.

The portion of each of the transfer tubes 30, which penetrates the analysis chains 20 traversing the biological protection enclosure 22, is oriented in a substantially vertical direction, so that the pots 12 drop into a receptacle incorporating a slide ring 36. The latter normally occupies a top position, in which it blocks the link between the tube 30 and the interior of the biological protection enclosure 22, which permits the displacement of the pots in the tube 30 under the action of the pump 34 and preserves the confinement of the vacuum atmosphere contained in the protection enclosure 22.

As soon as a not shown transducer detects the arrival of a pot on the receptacle 36 occupying said top position,,a lowering of the slide ring within the biological protection enclosure 22 is controlled from the central control unit 28. This can in particular be obtained with the aid of a not shown nozzle oriented in a horizontal direction and connected to a compressed air source, so as to inject compressed air over the receptacle 36 containing the pot 12.

In a first embodiment of the invention illustrated in greater detail in FIG. 2, the lower end of the slide ring 36 is fixed, e.g. by means of screws 38, to a horizontal support plate 40. The support plate 40 is perforated, in the extension of the slide ring 36, by a hole 41 used for fixing above the said plate 40 a force transducer designated in general terms by the reference 42.

More specifically, the force transducer 42 has a lower part 44, which is fixed above the support plate 40. For this purpose a nut 46 is screwed onto a threaded rod 48 belonging to the lower part 44 and traversing the hole 41 formed in the support plate 40. The seal between the lower part 44 of the force transducer 42 and the support plate 40 is ensured by an 0-ring 50 trapped between the two parts.

The force transducer 42 also has an upper part 52, mobile along the substantially vertical axis of the transducer within the bottom part of the slide ring 36. This top part 52 of the force transducer 42 is extended upwards along the axis of the slide ring 36 by a rod 54 carrying a disk 56 at its upper end.

Strain gauges (not shown in FIG. 2) are interposed between the upper part 52 and the lower part 44 of the force transducer 42, so that when a pot 12 rests on the disk 56, an electric measuring signal representative of the total weight of the pot 12 is emitted by said strain gauges. This signal is transmitted to an electronic measuring means 58 (FIG. 1) located at the end of the biological protection enclosure 22 by a cable 60.

When the pot weighing means constituted by the force transducer 42 and the electronic measuring means 58 associated therewith have the essential function of detecting the arrival of an empty or inadequately filled pot at any random one of the analysis chains 20, the measuring signal from the electronic measuring means 58 is transmitted to comparison means 62 (FIG. 1). Within said comparison means, the measuring signal is compared with a predetermined threshold below which it is considered that the pot 12 is empty or inadequately filled. If this is the case, an emptiness signal is emitted and transmitted by the comparison means 62 to the central control unit 28. The unit can then address the necessary instructions to the different members of the installation which it controls, so that a new sampling operation identical to that which should have been in the empty or inadequately filled pot is carried out and is again addressed to the corresponding analysis chain.

In a not shown constructional variant, the measuring signals supplied by the electronic measuring means 58 can be directly transmitted to the central control unit 28, so as to permit a quantitative control of each of the sampling operations carried out by the installation, so that only the radioactive liquid quantities just necessary for the analyses to be carried out are taken. The sample contained in each of the pots can then be used, at least in certain cases, for carrying out several different analyses of the same radioactive liquid. The measurement of the weight of each of the pots performed by the weighing means comprising the force transducer 42 and the associated electronic measuring means 58 makes it possible to calculate the sampled volumes, bearing in mind that the density of the sampled radioactive liquids is known. This constructional variant makes it possible to optimize the control of the waste produced by the installation, because the radioactive liquid quantities and the pots which are discarded after analysis can thus be minimized.

On again referring to FIG. 2, it can be seen that the upper part 52 of the force transducer 42 can move in a substantially vertical direction with respect to the lower part 44 between an upper tension abutment 55 and a lower compression abutment 57 formed on said latter part and limiting said displacement in one or other direction. This avoids damage to the transducer as a result of the shock produced by the high speed arrival of a pot 12 on the disk 56.

FIG. 2 also shows that when a pot 12 rests on the disk 56 within the slide ring 36, it faces a window 64 formed in the latter. Moreover, a nozzle 66, connected by a support 67 to the support plate 44, issues in a substantially horizontal direction from one side of the window 64. This nozzle 66 is connected by a flexible tube 68 to a compressed air source 70 (FIG. 1) located outside the biological protection enclosure 22.

The compressed air source 70 is controlled by the central control unit 28, so that compressed air escapes from the ejection nozzle 66 on completion of the weighing of the pot 12 with the aid of the aforementioned weighing means. The compressed air leaving the nozzle 66 has the effect of ejecting the pot 12 through the window 64, so as to drop on a not shown apparatus, such as a ramp or conveyor, making it possible to move the same up to the relevant analysis station of the chain or line 20.

Finally, in view of the fact that the pots 12 are most frequently made from a plastics material, which can be charged with static electricity during its transfer within the tubes 30, precautions are advantageously taken to ensure that said static electricity is not discharged on the force transducer 42, which could falsify its measurements.

For this purpose, a first solution consists of making the transducer 40 from a non-electricity conducting material, at least in that part of the disk 56 on which will rest the pot 12. Another solution consists of providing in the receptacle 36 or in the adjoining part of the tube 30, means for discharging the static electricity with which the pots 12 could be charged.

In a second embodiment of the invention illustrated in FIG. 3, the force transducer 42 is not connected to the slide ring 36, instead being connected to a fixed part, such as the part of the transfer tube 30, which descends vertically into the analysis chain 20. Moreover, the force transducer 42 is laterally and downwardly displaced with respect to the slide ring 36. These characteristics make it possible to very significantly reduce the shocks suffered by the transducers during the arrival of the pots and consequently brings about a significant reduction in the failure risks of said transducers due to shocks.

More specifically, the force transducer 42 is fitted vertically in a recess 72 formed in a protection box or casing 74, which is connected to the lower end of the transfer tube 30 by a rigid structure 76. Moreover, the vertical axis of the recess 72 is laterally displaced with respect to the vertical axis of the lower end of the tube 30.

Moreover, the slide ring 36 has on its upper face an inclined ramp 78, turned towards the recess 72. A guide funnel 80 joined to the ring 36, e.g. by screws 82, is placed above the recess 72, in the extension of the inclined ramp 78. The slide ring 36 and the funnel 80 constitute a mobile assembly between an upper position (illustrated in mixed lines in FIG. 3) and a lower position illustrated in continuous line form.

In the upper position of said mobile assembly, the ramp 78 closes the tube 30 at its lower end and the funnel 80 is spaced from the force transducer 42 by a distance at least equal to the height of a pot 12. A not shown compressed air nozzle identical to the nozzle 66 in FIG. 2 and issuing above the protection case 74 then makes it possible to discharge the pot 12 following its weighing.

In the lower position of the mobile assembly, the pot 12 descends by gravity on the inclined ramp 78 and enters the funnel 80, so as to rest without impact on the force transducer 42.

In the embodiment illustrated in FIG. 3, the mobile assembly is guided by a vertical post 84, integral with the slide ring 36 and received in guide lugs 86 integral with the tube 30.

When a pot 12 arrives in the analysis chain, the assembly formed by the slide ring 36 and the funnel 80 is in the top position and closes the tube 30. The descent of this assembly opens the tube 30 and permits the descent by gravity of the pot up to the force transducer 42. When weighing has taken place, the assembly constituted by the slide ring 36 and the funnel 80 rises again. The pot 12 can then be discharged by a compressed air jet.

The automated pot transfer installation described hereinbefore with reference to FIGS. 1 to 3 makes it possible to weigh the pots when they arrive in each of the analysis chains, which, as has been shown hereinbefore, allows an immediate new sample to be taken in the case of a defective sampling operation and/or a stricter checking of the liquid and solid waste passing out of the different analysis chains.

Moreover, the particular installation of the weighing means described hereinbefore makes it unnecessary to provide around them a supplementary neutron protection and authorizes a risk-free intervention in the case of a system failure.

Finally, the operating speed of the installation is virtually not reduced by the introduction of the weighing means, because between two consecutive pots moving within the tubes there is an adequate distance to enable the weighing and ejection of one of them to take place before another pot reaches the weighing means.

Obviously, the invention is not limited to the embodiment described in exemplified manner hereinbefore and covers all variants thereof. Thus, it is clear that the transfer installation according to the invention can have a random number of sampling units and analysis chains. Moreover, these sampling units and analysis chains can be produced in a random manner without passing outside the scope of the invention. In the same way, the vacuum pot distribution stations, the switches provided in the transfer tubes and the means for the pneumatic transfer of the pots within these tubes can be produced in a random manner.

We claim:

1. An automated installation for the transfer of pots containing a radioactive liquid sample, from at least one automatic sampling unit to at least one analysis chain, said installation comprising:

a pot receptacle placed within a confined enclosure of each analysis chain, said receptacle including automatic weighing means for weighing the pots;

tubes connecting each automatic sampling unit to each receptacle;

pneumatic transfer means for the transfer of the pots into the tubes; and a central unit controlling said automatic sampling unit and said pneumatic transfer means.

2. Installation according to claim 1, wherein the receptacle comprises a substantially vertically axed slide ring and the weighing means comprise a force transducer fitted at a lower end of the slide ring.

3. Installation according to claim 1, wherein the receptacle comprises a substantially vertically axed slide ring and a funnel integral therewith, the funnel being laterally and downwardly displaced with respect to the slide ring, the slide ring having a lower ramp oriented towards the said funnel and wherein the weighing means comprise a force transducer fitted to a fixed support below the funnel.

4. Installation according to either of the claims 2 and 3, wherein the force transducer has a lower reference part and an upper part which is vertically mobile relative to the lower part and which can bear against upper and lower abutment surfaces of the lower part when a force exceeding a tolerance threshold of the transducer is respectively exerted upward and downwards on the upper part.

5. Installation according to either of the claims 2 and 3, wherein the weighing means also incorporate an electronic measuring means positioned outside the confined enclosure and a cable traversing the enclosure and connecting the measuring means to the force transducer.

6. Installation according to claim 1, wherein the pot ejection nozzle is fitted to each of the receptacles and a compressed air source controlled by the central unit and connected to the nozzle.

7. Installation according to claim 1, further comprising comparison means which are able to compare a measuring signal supplied by the weighing means with a given threshold, said comparison means addressing an emptiness signal to the central unit when the measuring signal is below said threshold.

8. Installation according to claim 7, wherein the central unit controls a new sampling operation identical to the missing sampling operation, on receiving an emptiness signal.

9. Installation according to claim 1, wherein the pots are made from a material which can be charged with static electricity, and a disk is provided on the weighing means for receiving the pots, which disk is made, at least on its surface, from an electrically insulating material.

10. Installation according to claim 1, wherein the pots are made from a material which can be charged with static electricity, and means for discharging the static electricity are provided in the receptacle above the weighing means.

* * * * *